US012742788B1

(12) United States Patent
Morin et al.

(10) Patent No.: US 12,742,788 B1
(45) Date of Patent: Sep. 22, 2026

(54) EQUINE MULTIPLEX HEALTH INFORMATION PANEL

(71) Applicant: Boundless Diagnostics Inc, Portland, ME (US)

(72) Inventors: Trevor Morin, Scarborough, ME (US); Josh Hayward, Bangor, ME (US); Kevin Grant, Bridgewater, MA (US)

(73) Assignee: Boundless Diagnostics Inc, Portland, ME (US)

( * ) Notice: Subject to any disclaimer, the term of this patent is extended or adjusted under 35 U.S.C. 154(b) by 0 days.

(21) Appl. No.: 19/337,507

(22) Filed: Sep. 23, 2025

(51) Int. Cl.
*G01N 33/68* (2006.01)
*G06N 3/0455* (2023.01)

(52) U.S. Cl.
CPC ....... *G01N 33/6893* (2013.01); *G06N 3/0455* (2023.01); *G01N 2333/5412* (2013.01); *G01N 2333/96494* (2013.01)

(58) Field of Classification Search
None
See application file for complete search history.

(56) References Cited

U.S. PATENT DOCUMENTS

| | | | | |
|---|---|---|---|---|
| 9,176,126 B2 | | 11/2015 | Holmes | |
| 9,772,291 B2 | | 9/2017 | Kemp | |
| 2004/0058456 A1 | * | 3/2004 | Safsten | B01J 19/0046 427/2.11 |
| 2004/0229226 A1 | * | 11/2004 | Reddy | G01N 33/54373 506/13 |
| 2006/0246599 A1 | * | 11/2006 | Rosenstein | G01N 33/54388 436/514 |
| 2008/0032420 A1 | * | 2/2008 | Lambert | G01N 33/54388 436/514 |
| 2011/0008799 A1 | * | 1/2011 | Kiernan | G01N 33/6893 435/7.1 |
| 2011/0207622 A1 | * | 8/2011 | Wong | C12Q 1/6886 435/7.1 |
| 2016/0069870 A1 | * | 3/2016 | Ueya | G01N 33/545 436/501 |

FOREIGN PATENT DOCUMENTS

CA 3058871 A1 * 10/2018 ....... G01N 33/54388

OTHER PUBLICATIONS

Arufso et al., Inflammatory-like status and acute stress response in horses after road transport, Scientific Reports, 13(9858), (2023), 11 pages. (Year: 2023).*

Dondi et al., Serum amyloid A, haptoglobin, and ferritin in horses with colic: Association with common clinicopathological variables and short-term outcome, The Veterinary Journal, 205, (2015), p. 50-55. (Year: 2015).*

Knoepfli et al., Extertional rhabdomyolysis in a 4-year-old standardbred filly, Can. Vet. J., 43, (2002), p. 293-295. (Year: 2002).*

Rabelo, Isabela et al., "Acute phase proteins levels in horses, after a single carbohydrate overload, associated with cecal alkalinization" Frontiers in Veterinary Science, 2023. Download Available at https://www.frontiersin.org/journals/veterinary-science/articles/10.3389/fvets.2023.1043656/full.

Oke, Stacey et al., "Practical Uses of Serum Amyloid A in Horses" EquiManagement, Jun. 23, 2025. https://equimanagement.com/research-medical/diagnostics/practical-uses-of-serum-amyloid-a-in-horses/.

Witkowska-PiłaszewiczO.etal., "Serum amyloid A in equine health and disease" PMC Review, Feb. 2019. PMC https://pmc.ncbi.nlm.nih.gov/articles/PMC7163734/.

"Carvalho Filho W. P. et al., "Serum amyloid A and muscle activity biomarkers inhorses submitted to equestrian show jumping" Brazilian Journal of Veterinary Research, Aug. 2019. SciELO. pp. 668-672, 4 pages. https://www.scielo.br/j/pvb/a/VCLrk83HQCWphrpRmdBtzjb/?format=pdf&lang=en".

"Giers, J. et al., "Blood-Based Markers for Skeletal and Cardiac Muscle Functionin Eventing Horses before and after Cross-Country Rides andHow They Are Influenced by Plasma Volume Shift," MDPI, 2023. Download available by PMC. https://pmc.ncbi.nlm.nih.gov/articles/PMC10572052/".

Billings, A. et al, Oct. 20, 2022, "Veterinary Laboratory Markers of Muscle Injury" Veterian Key. https://veteriankey.com/laboratory-markers-of-muscle-injury/.

"Cerón, J. et al., "S-100 Proteins: Basics andApplications as Biomarkers inAnimals with Special Focus onCalgranulins (S100A8, A9, andA12)" MDPI, 2023. published Jun. 19, 2023. https://www.mdpi.com/2079-7737/12/6/881".

Muñoz-Prieto A et al., "Changes in Calprotectin (S100A8-A9) and Aldolase in the Saliva of Horses with Equine Gastric Ulcer Syndrome" Published Apr. 16, 20233. MDPI. Download Available at https://www.mdpi.com/2076-2615/13/8/1367.

López-Martínez M J et al., "Changes in salivary biomarkers of stress, inflammation, redox status, and muscle damage due to *Streptococcus* suis infection in pigs" BMC Veterinary Research, 19:100. 9 pages. 2023. Download available at https://pmc.ncbi.nlm.nih.gov/articles/PMC10388462/.

Canatu. "Canatu CNT Material Transforming diagnostics with exceptional sensitivity" 2024. 17 pages.

Sekhwama, Masindi. "Integration of microfluidic chips with biosensors" Published Aug. 23, 2024, Discover Applied Sciences. (2024)6:458. 32 pages. https://doi.org/10.1007/s42452-024-06103-w.

* cited by examiner

*Primary Examiner* — Ellen J Marcsisin
(74) *Attorney, Agent, or Firm* — Talem IP Law, LLP

(57) ABSTRACT

Disclosed are equine biomarker panels and methods for generating actionable health and training guidance from multiplex biochemical measurements. The panel is organized across physiologic axes: core inflammation (e.g., CRP, SAA, IL-6, S100A8/A9, IRF7), muscle/tissue injury and metabolic stress (e.g., lactate, CK, AST, LDH, myoglobin, ADAM-12), trauma/stress (e.g., HMGB1, haptoglobin, cortisol), and oxidative/joint/cartilage status (e.g., 8-isoprostane, COMP, MMP-3, MMP-8, ferritin). Quantitative values from an equine sample are combined into composite indices and/or ratiometric measures, optionally classified against subject-specific baselines and population references to produce readiness or risk categories. The method then outputs protocol-ready actions including training-load modification, rest or return-to-work guidance, re-test intervals, imaging/referral prompts, and selection of supplementation categories.

2 Claims, 1 Drawing Sheet

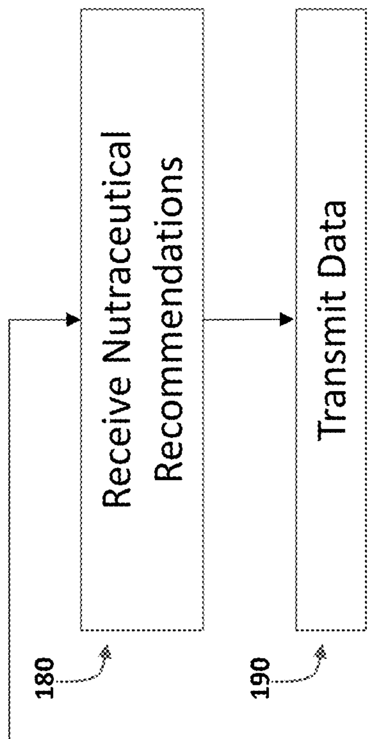
Receive Nutraceutical Recommendations
Transmit Data
180
190
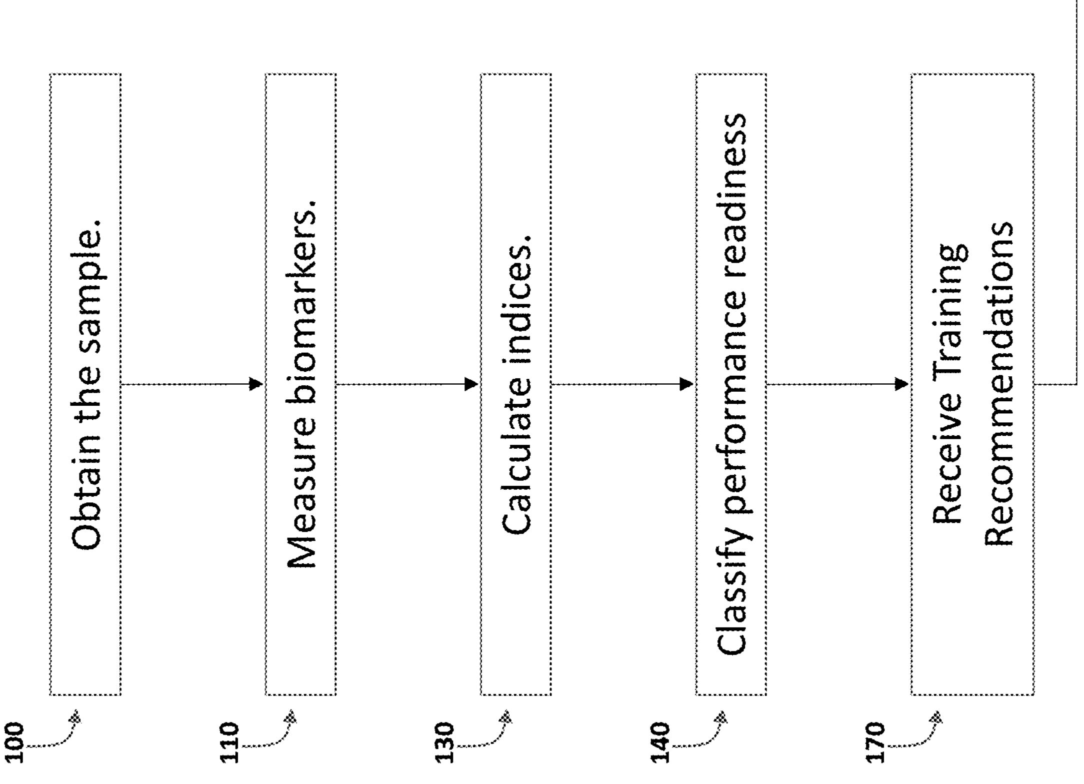
Obtain the sample.
Measure biomarkers.
Calculate indices.
Classify performance readiness
Receive Training Recommendations
100
110
130
140
170

EQUINE MULTIPLEX HEALTH INFORMATION PANEL

FIELD

This disclosure relates to biomarker panels and interpretation methods for generating actionable equine health and training guidance from multiplex biochemical measurements.

BACKGROUND

Equine performance management benefits from simultaneous consideration of systemic inflammation, muscle/tissue injury, trauma/stress, oxidative status, and joint/cartilage turnover. Conventional workflows often evaluate only a subset of relevant markers, leading to delayed or fragmented decision-making about training load, recovery, and supplementation. A defined, cross-system biomarker panel, interpreted with transparent rules or learned models, can standardize assessments and produce clear, protocol-ready outputs.

SUMMARY

Disclosed herein are: (i) an equine biomarker panel definition organized across specific physiologic axes and (ii) methods of providing actionable equine health information using results from that panel. Measurements may be obtained by any suitable analytical technique (e.g., immunoassay, aptamer switch assay, particle/resonator imaging, lab or point-of-care). The measurements use techniques that employ reagents, where, in embodiments, the reagents may be antibody capture reagents, antibody or fragment detection reagents, aptamer or aptamer-switch elements, and/or particle-conjugated detection reagents.

In embodiments, measured values are normalized (e.g., to subject baselines and/or population references), combined into composite indices and/or ratiometrics, classified into readiness/risk categories, and mapped to recommended actions that include training-load modification, rest/return-to-work guidance, re-test intervals, referral prompts, and nutraceutical category selections.

Specifically, one embodiment provides an equine multiplex biomarker panel, comprising an assay reagent set including a plurality of affinity reagents and/or aptamer elements configured to specifically bind and enable quantitative detection, in an equine biological sample, each of a respective set of biomarkers selected from: (i) Core Inflammation: C-reactive protein (CRP), serum amyloid A (SAA), interleukin-6 (IL-6), S100A8/A9 (calprotectin), interferon regulatory factor 7 (IRF7); (ii) Muscle or Tissue Injury and Metabolic Stress: lactate, creatine kinase (CK), aspartate transaminase (AST), lactate dehydrogenase (LDH), myoglobin, ADAM-12; (iii) Trauma or Stress: high-mobility group box 1 (HMGB1), haptoglobin, cortisol; and (iv) Oxidative and Joint/Cartilage Status: 8-isoprostane, cartilage oligomeric matrix protein (COMP), matrix metallopeptidase-3 (MMP-3), matrix metallopeptidase-8 (MMP-8), ferritin; wherein the set of biomarkers includes at least one biomarker from at least two of categories (i) through (iv).

Another embodiment provides such a panel, wherein the set of biomarkers includes at least one biomarker from each of categories (i) through (iv), above.

A further embodiment provides such a panel, wherein the set of biomarkers comprises all of the following biomarkers: CRP, SAA, IL-6, S100A8/A9, IRF7, lactate, CK, AST, LDH, myoglobin, ADAM-12, HMGB1, haptoglobin, cortisol, 8-isoprostane, COMP, MMP-3, MMP-8, and ferritin.

Yet another embodiment provides such a panel, wherein the assay reagent set comprises, for each targeted biomarker, at least one of: an antibody capture reagent, an antibody or fragment detection reagent, an aptamer or aptamer-switch element, or a particle-conjugated detection reagent.

A yet further embodiment provides such a panel, wherein the reagents are formulated for simultaneous multiplex measurement in a single run from whole blood, serum, plasma, saliva, perspiration, fecal eluate, or urine, and wherein the capture reagents of the panel are immobilized on a solid phase comprising discrete capture regions arranged as a multiplexed array on a substrate.

One embodiment provides a method of providing actionable equine health information, comprising: (a) obtaining a biological sample from an equine subject, the sample selected from whole blood, serum, plasma, saliva, urine, perspiration, or a fecal eluate; (b) obtaining quantitative measurements for a set of biomarkers from the biological sample, the set comprising biomarkers drawn from at least two of the following categories: (i) Core Inflammation: CRP, SAA, IL-6, S100A8/A9, and IRF7; (ii) Muscle or Tissue Injury and Metabolic Stress: lactate, CK, AST, LDH, myoglobin, and ADAM-12; (iii) Trauma or Stress: HMGB1, haptoglobin, and cortisol; and (iv) Oxidative and Joint/Cartilage Status: 8-isoprostane, COMP, MMP-3, MMP-8, and ferritin; (c) computing one or more indices and/or ratiometric measures from the measurements, the indices including at least one of: an inflammation index, a muscle damage index, a trauma or stress index, and an oxidative/joint index; (d) optionally classifying the subject into a readiness or risk category based on the indices and/or changes from a subject-specific baseline and/or population reference distributions; and (e) outputting an actionable recommendation comprising at least one of: training-load modification, rest or return-to-work guidance, re-test interval, referral or imaging prompt, and selection of a supplementation category.

A still further embodiment provides such a method, wherein the set of biomarkers includes at least one biomarker from each of categories (i) through (iv).

Even another embodiment provides such a method, wherein classifying comprises assigning the subject to one of ready, conditional (modify load), or not ready (rest/diagnose).

An even further embodiment provides such a method, wherein the actionable recommendation includes selection of a supplementation category chosen from: Core Inflammation, Muscle/Tissue Injury, Trauma & Stress, Oxidative Stress, and Joint Health/Cartilage, with optional dosage, timing, and duration guidance.

The features and advantages described herein are not all-inclusive and, in particular, many additional features and advantages will be apparent to one of ordinary skill in the art in view of the drawings, specification, and claims. Moreover, it should be noted that the language used in the specification has been selected principally for readability and instructional purposes, and not to limit the scope of the inventive subject matter.

BRIEF DESCRIPTION OF THE DRAWINGS

FIG. 1 is a flow chart depicting a method for using an equine multiplex health information panel according to the present disclosure to obtain actionable equine health information.

DETAILED DESCRIPTION

One aspect of the present disclosure relates to an equine multiplex health information panel spanning at least two, and preferably three or more, of the following categories, with analytes listed for each category:

- Core inflammation: C-reactive protein (CRP), serum amyloid A (SAA), interleukin-6 (IL-6), S100A8/A9 (calprotectin), interferon regulatory factor 7 (IRF7).
- Muscle/tissue injury & metabolic stress: lactate, creatine kinase (CK), aspartate transaminase (AST), lactate dehydrogenase (LDH), myoglobin, ADAM-12.
- Trauma/stress: high-mobility group box 1 (HMGB1), haptoglobin, cortisol.
- Oxidative & joint/cartilage: 8-isoprostane, cartilage oligomeric matrix protein (COMP), matrix metallopeptidase-3 (MMP-3), matrix metallopeptidase-8 (MMP-8), ferritin.

These enumerated analytes (biomarkers) are selected to capture orthogonal physiological axes (inflammation, muscle/tissue injury, trauma/stress, oxidative/joint) whose combined patterns provide superior training readiness discrimination versus any single axis alone.

In embodiments, the panel is provisioned including all listed analytes to maximize cross-system coverage, while in other embodiments reduced configurations preserve cross-category balance by including at least one marker from each of core inflammation, muscle/tissue injury, and oxidative/joint status so that readiness can still be resolved with minimal assay burden. In yet other embodiments targeted add-ons are appended to refine specific analyses, for example, ADAM-12 to weight muscle remodeling versus acute damage, or IRF7 to help differentiate infectious from non-infectious inflammatory load.

In embodiments, results obtained from the panel are interpreted through a combination of rules and statistical or machine-learning models that transform raw measurements into decision-ready outputs. The processor may first derive composite indices, such as an inflammation index, a muscle-damage index, and an oxidative/joint index, together with ratiometric features and deltas that include, by way of example, CK/AST, percent change from an individual baseline, and z-scores relative to population reference bands. These features are then used to assign a readiness or risk classification (e.g., ready, conditional (modify load), or not ready (rest/diagnose)) and to generate explicit action mappings that specify next steps, such as adjusting training load, scheduling a re-test window, initiating imaging or referral, and selecting an appropriate supplementation category from Core Inflammation, Muscle/Tissue Injury, Trauma & Stress, Oxidative Stress, or Joint Health/Cartilage.

By way of illustration and without limitation, when SAA, CRP, or IL-6 is elevated together with a concurrent spike in CK or myoglobin, the system may recommend reduced workload, prioritize supplementation from the Core Inflammation and Muscle/Tissue Injury categories, and set a short re-test interval. When HMGB1 is elevated alongside cortisol and 8-isoprostane, the subject may be classified as experiencing stress/trauma with oxidative burden; the recommendation may emphasize Trauma & Stress and Oxidative Stress support and an extended recovery window. When COMP and/or MMP-3/MMP-8 trend upward from baseline, the system may flag joint risk, prompt adjustments to surface or footing, suggest Joint Health/Cartilage support, and recommend imaging or referral. When ferritin is abnormal in conjunction with elevated lactate, the guidance may be for reduced workload, added antioxidant support, and a review of mineral status.

In embodiments, longitudinal analytics are maintained to contextualize each measurement in time. Subject-specific baselines are established and updated; trend detection methods such as exponentially weighted moving averages, cumulative-sum control charts, and change-point analyses are applied; and event-linked comparisons are performed around training sessions, dosing, or other relevant milestones so that recommendations reflect both current status and trajectory.

Measurements may be obtained using any suitable analytical approach capable of producing quantitative values for the specified analytes in equine samples, including but not limited to blood, serum, plasma, saliva, perspiration, fecal matter, or urine. Suitable analytical approaches include, but are not limited to, enzyme- or affinity-based immunoassays (ELISA, lateral-flow, chemiluminescent and electrochemiluminescent formats), time-resolved fluorescence (lanthanide TRF) and FRET/TR-FRET assays, aptamer-switch and other nucleic-acid-based affinity assays, multiplex bead or planar microarrays, proximity ligation/extension assays with qPCR or next-generation sequencing readouts, label-free optical biosensing (e.g., surface plasmon resonance, biolayer interferometry, photonic resonators/interferometric waveguides), particle-enhanced optical imaging (e.g., gold-nanoparticle labels with resonator contrast), electrochemical biosensing (amperometric, voltammetric, impedimetric), electrical biosensing (e.g., carbon nanotubes, graphene field effect transistor), including enzymatic oxidase/peroxidase assays for metabolites such as lactate, chromatographic and mass-spectrometric methods (HPLC/UPLC with UV/fluorescence detection, LC-MS/MS, GC-MS) with optional immunoaffinity enrichment, capillary electrophoresis, and microfluidic lab-on-chip implementations of any of the foregoing, in central-laboratory or point-of-care formats, individually or in combination.

In nonlimiting embodiments, the panel is provided as a reagent set formulated to permit simultaneous multiplex measurement in a single run from whole blood, serum, plasma, saliva, perspiration, fecal eluate, or urine. Capture reagents (e.g., antibodies, fragments, engineered binders, or aptamers) are immobilized on a solid phase in discrete capture regions arranged as a multiplexed array on a substrate. Suitable substrates include, without limitation, functionalized glass or silica slides, polymeric films, nitrocellulose or other porous membranes, and hydrogel-coated surfaces. Immobilization chemistries may comprise passive adsorption on nitrocellulose; covalent tethering via aldehyde/epoxy-silane or NHS-ester functionalized glass; carbodiimide coupling (EDC/NHS) to carboxylate-bearing hydrogels; or click-type linkages for pre-modified capture ligands (amine, thiol, azide/alkyne, acrydite). Capture features may be patterned by contact pin or piezoelectric micro-spotting to spot volumes of ~50-500 μL per feature with inter-spot spacing of ~200-1000 μm (non-limiting), and may be bounded by hydrophilic/hydrophobic patterning or shallow physical baffles to limit cross-talk. Arrays include per-panel positive controls (e.g., species-matched IgG targets or tagged calibrators) and negative controls (blocking buffer only) for QC gating.

To make the array, in embodiments the substrate is cleaned/activated, functional groups are applied (e.g., epoxy-silane), capture ligands are dispensed at target densities (e.g., 0.05-0.5 mg/mL spotting solutions), incubated for covalent coupling or adsorption, then blocked (e.g., 1-3% BSA/casein) and dried under controlled humidity. Arrays may be packaged with desiccant and lot-coded.

To use the panel in a single run, in embodiments a defined volume (e.g., 10-200 μL; non-limiting) of sample from any of the listed matrices is contacted with the multiplexed array under binding conditions for a fixed incubation interval; the array is washed to remove unbound material; the multiplex detection cocktail is applied (or rehydrated in situ if pre-deposited), followed by a final wash and readout appropriate to the chosen labels (e.g., gated excitation/emission collection for TRF/TR-FRET; spectral imaging; or resonator/particle contrast imaging). Quantitation may be performed against the provided calibrators using fit models (e.g., 4PL/5PL for intensity-based assays; linear regions for particle counts), with QC acceptance enforced by control features. Because capture features for all targeted biomarkers are co-located on the same substrate and the detection mixture is formulated to be mutually compatible, all biomarkers are measured simultaneously in the same run regardless of matrix. The resulting per-analyte values are suitable for downstream computation of panel-level indices, ratiometrics, and classifications as described elsewhere, agnostic to any particular cartridge or reader architecture beyond a detector capable of resolving the selected labels. Alternative workflows are realized as well. For example, a volume of sample can contact detection reagent (liquid or dried/lyophilized), followed by incubation with the multiplex array, a follow-on wash step may be employed or not, and the signal read providing a quantitative value by using pre-qualified (i.e., during time of manufacture) calibration curve. In another embodiment, calibration molecules at known concentration, which do not exist in the sample, are included in the testing thereby allowing an in-run standard curve during each test cycle.

For avoidance of doubt, the "panel" as used herein is not limited to any particular article or format and encompasses any composition or kit configured for multiplex measurement of the recited biomarkers, including (without limitation) pre-arrayed solid phases, lyophilized or liquid detection cocktails, calibrators and controls, buffers and blockers, and capture/detection reagents supplied in one or more containers, whether physically co-packaged, bundled under a common SKU, co-labeled or co-sold for combined use, or otherwise distributed with instructions indicating joint use in a single assay run (simultaneous or sequential).

Another aspect of the present disclosure is a method for providing actionable equine health information by first obtaining a biological sample from an equine subject (such as whole blood (e.g., venipuncture) or capillary puncture (lancet-based microsampling), serum, plasma, saliva, perspiration, urine, or a fecal eluate), optionally performing minimal pre-analytical processing (e.g., dilution, separation, stabilization) and recording sample metadata (subject ID, time of draw, fasting status, and event markers such as training or dosing); obtaining quantitative measurements for a set of biomarkers drawn from at least two of the following categories: Core Inflammation (e.g., CRP, SAA, IL-6, S100A8/A9, IRF7), Muscle or Tissue Injury and Metabolic Stress (e.g., lactate, CK, AST, LDH, myoglobin, ADAM-12), Trauma or Stress (e.g., HMGB1, haptoglobin, cortisol), and Oxidative and Joint/Cartilage Status (e.g., 8-isoprostane, COMP, MMP-3, MMP-8, ferritin); followed by computing panel-level indices and/or ratiometric measures (including deltas from a subject-specific baseline and/or z-scores versus population reference intervals), optionally classifying the subject into a readiness or risk category, and outputting an actionable recommendation comprising one or more of: training-load modification, rest or return-to-work guidance, re-test interval, referral or imaging prompt, and selection of a supplementation category with optional dosage, timing, and duration parameters, wherein measurements may be acquired by any suitable analytical approach and interpretation may be performed by rule-based logic and/or learned models.

In embodiments, a supplementation category may be selected from, for example, those shown in Table 1, below, based on panel-level indices and/or ratiometric measures resulting from the panel measurements.

TABLE 1

| Panel-level Index | Supplementation Category | Example Ingredients |
|---|---|---|
| Core Inflammation | Anti-inflammatory & immune-modulating | Omega-3s, turmeric, boswellia, vitamin E |
| Muscle/Tissue Injury | Muscle recovery & antioxidant support | Vitamin E, selenium, BCAAs, L-carnitine, MSM |
| Trauma & Stress | Adaptogens & stress recovery blends | Ashwagandha, magnesium, B-vitamins, antioxidants |
| Oxidative Stress | Antioxidant-rich formulas | Vitamin E, vitamin C, selenium, NAC, polyphenols |
| Joint Health/Cartilage Damage | Joint support & cartilage protection | Glucosamine, chondroitin, hyaluronic acid, collagen, MSM |

In embodiments, quantitative measurements are acquired for an equine subject across a multi-analyte set drawn from the specified categories using any assay capable of producing calibrated values in equine matrices (e.g., blood/serum/plasma, saliva, urine, perspiration). The measurements are processed by a data processor or external computing resource to (i) compute composite indices (e.g., an Inflammation Index aggregating CRP, SAA, IL-6, S100A8/A9 and/or IRF7; a Muscle-Damage Index aggregating lactate, CK, AST, LDH, myoglobin, and/or ADAM-12; an Oxidative/Joint Index aggregating 8-isoprostane, COMP, MMP-3, MMP-8, and/or ferritin) and (ii) compute ratiometric measures such as CK/AST and percent change from subject-specific baselines and/or standardized z-scores against population reference bands. The processor may employ statistical and machine-learning methods (e.g., regularized regression, gradient boosting, distance-based discrimination) to map the multi-analyte feature vector, including raw values, ratiometrics, and longitudinal deltas, into categorical or probabilistic outputs. Trends and event-linked comparisons (pre/post training or dosing) can be generated automatically to refine readiness/risk assessment and to distinguish normal from abnormal variation. The system may then output an actionable recommendation comprising one or more of: training-load modification, rest or return-to-work guidance, re-test interval, referral/imaging prompt, and selection of a supplementation category, which may be delivered to a local display or exported to external information systems.

In embodiments, classification into "ready," "conditional (modify load)," or "not ready (rest/diagnose)" is produced by applying rule-based and/or model-based logic to the computed indices and deltas. For example, non-limiting rules may include the following:

Elevated SAA/CRP/IL-6 together with a CK or myoglobin spike→reduce training load and set a short re-test interval HMGB1 with cortisol elevated in the presence of increased 8-isoprostane→stress/trauma with oxidative burden, extend recovery Rising COMP and/or MMP-3/MMP-8 above baseline→joint-risk flag and surface/footing adjustments with possible imaging.

In embodiments, population reference distributions and subject-specific baselines are used to generate z-scores and percent changes to increase specificity, while subject-specific trend detectors may distinguish acute from chronic load.

In embodiments, biomarkers may be substituted by functional equivalents within the same pathway or physiologic axis that provide substantially similar interpretive value without departing from the disclosed framework. Substitution is implemented by (i) calibrating the equivalent marker to the panel's reference scales, (ii) updating index coefficients or rules to incorporate the equivalent's expected directionality and dynamic range, and (iii) validating distribution-aware calls (e.g., z-scores, percentile bands) and multivariate thresholds to maintain classification performance across cartridges, lots, and instruments via calibration transfer/domain adaptation. In embodiments, the functional equivalent is (A) within the same biological pathway or physiologic axis as the replaced biomarker and (B) demonstrates at least one of: (i) Pearson correlation ≥0.60 to the replaced biomarker across a validation cohort under the same sampling/assay conditions; or (ii) an AUROC within 10% (absolute) of the replaced biomarker for a predefined readiness/risk classification task using the same model and dataset.

In certain embodiments, equine health information may be acquired and equine performance readiness may be evaluated through the following method steps, as depicted in FIG. 1.

Obtaining the Sample. A biological sample is obtained 100 from an equine subject. Suitable sample types include blood, serum, plasma, urine, saliva, or perspiration, each providing access to relevant biomarker concentrations.

Measuring Biomarkers. The sample is analyzed 110 to measure quantitative levels of biomarkers from at least the following categories: (i) inflammation markers; (ii) muscle or tissue injury markers; (iii) trauma or stress markers; and (iv) oxidative or joint markers. The measurements may be obtained using a cartridge-based analyte detecting system configured for multiplex detection. In certain embodiments, the inflammation markers include at least one of C-reactive protein (CRP), serum amyloid A (SAA), interleukin-6 (IL-6), or S100A8/A9 (calprotectin), and/or IRF7 (interferon regulatory factor 7). The muscle or tissue injury markers may include lactate, creatine kinase (CK), aspartate transaminase (AST), lactate dehydrogenase (LDH), myoglobin, and/or ADAM metallopeptidase domain 12 (ADAM-12). The trauma or stress markers may include high-mobility group box 1 (HMGB1), haptoglobin, and/or cortisol. The oxidative or joint markers may include 8-isoprostane, cartilage oligomeric matrix protein (COMP), matrix metallopeptidase-3 (MMP-3), matrix metallopeptidase-8 (MMP-8), and/or ferritin.

Calculating Indices. In embodiments, the measured values are processed 130 to calculate biomarker ratios, composite scores, or indices across at least two of the biomarker categories. Such calculations may involve normalization to reference standards, weighting of categories, or statistical combination of biomarker signals.

Classifying Performance Readiness. Based on the calculated biomarker ratios, composite scores, or indices, the equine subject is classified 140 as performance-ready or not performance-ready. In embodiments, classification is determined by evaluating multivariate patterns across categories of biomarkers, including inflammation, muscle/tissue injury, trauma/stress, oxidative stress, and joint health. In embodiments, this classification step incorporates rule-based logic applied to biomarker trends. For example, if there is elevated SAA, CRP, or IL-6 indicating systemic inflammatory load, and concurrent CK or myoglobin spikes indicative of acute muscle strain, then the classification algorithm may determine that the animal is not performance-ready and that the training load should be reduced. In such a scenario, supplementation may be recommended from the Muscle/Tissue Injury category in Table 1 (e.g., Vitamin E, selenium, BCAAs, L-carnitine, MSM) together with Core Inflammation interventions (e.g., Omega-3s, turmeric, boswellia, Vitamin E). As another example, if HMGB1 and cortisol are elevated in combination with oxidative stress markers such as 8-isoprostane, then the classification may assign the subject to a "high stress/trauma load" category. Nutraceutical recommendations in this case may be drawn from the Trauma & Stress category of Table 1 (e.g., ashwagandha, magnesium, B-vitamins, antioxidants) together with Oxidative Stress interventions (e.g., Vitamin E, Vitamin C, selenium, NAC, polyphenols). Similarly, if COMP or MMP-3 values rise significantly above baseline or population-level reference ranges, the classification may shift the subject into a "joint risk" category, prompting recommendations from the Joint Health/Cartilage Damage group of Table 1 (e.g., glucosamine, chondroitin, hyaluronic acid, collagen, MSM). Classification may further include comparison to reference data sets derived from populations of equine subjects, ensuring context-sensitive interpretation. The biomarker profile may be compared to a longitudinal baseline from the same animal to determine supplementation adjustments over time, enabling personalized intervention strategies. Population-level comparisons allow the subject to be classified into defined readiness or risk categories (e.g., low risk/high readiness, moderate risk/conditional readiness, high risk/not performance-ready), each linked to specific nutraceutical guidance as outlined in Table 1.

Outputting Results. The classification results are output 150 to a display, transmitted to an external device, or integrated into an information system such as a stable management platform or veterinary electronic record. In some embodiments, the classification is based on a comprehensive panel of quantitative measurements that includes CRP, SAA, IL-6, S100A8/A9, IRF7, lactate, CK, AST, LDH, myoglobin, ADAM-12, HMGB1, haptoglobin, cortisol, 8-isoprostane, COMP, MMP-3, MMP-8, and ferritin, and functional equivalents thereof.

Receiving Training Recommendations. The system may further generate 170 actionable recommendations based on the classification results, including training modifications, rest periods, or dietary adjustments to optimize equine health and performance.

Receiving Nutraceutical Recommendations. Based on the classification result, in embodiments a supplementation recommendation is output 180 to a display, a mobile device, or an information management system. In embodiments recommendations may include antioxidant formulations, joint support formulations, adaptogen blends, electrolyte replenishment, gastrointestinal support, metabolic support, or immune modulation. In certain embodiments, the supplementation recommendation further specifies dosage, timing, and duration instructions tailored to the performance animal.

Data Transmission. Supplementation recommendations may be transmitted 190 to a veterinary practice management system, a cloud-based data storage service, or another external system to facilitate integration with broader care workflows.

As used herein, "panel" means an assay reagent set including a plurality of affinity reagents and/or aptamer elements configured to specifically bind and enable quantitative detection, in an equine biological sample, of a set of two or more biomarkers (including functional equivalents, isoforms, fragments, or surrogate measures) obtained from a subject and interpreted together as a unit to yield individual values and combined outputs, such as ratios, composite indices, scores, risk bands, or classifications, that inform equine health or performance status; the term is agnostic to sample matrix, analytical technique, and instrument, and encompasses fixed or configurable sets, as well as subsets, supersets, or substitutions by functional equivalents that provide substantially similar interpretive value.

As used herein, "biomarker" means a measurable molecular feature indicative of a physiological, pathological, or stress state.

As used herein, "reagent" (either capture or detection), may be full-length monoclonal antibodies, polyclonals, Fab fragments, $F(ab')_2$ fragments, scFv, or other affinity proteins provided that binding specificity is retained. Reagents may be full length proteins or protein complexes, or smaller domains or sub-domains of proteins, or MIPS (molecular imprinted proteins or polymers). Additionally, reagents may bind particular chemical groups present on a target analyte, e.g., the use of lectins to bind glycosylated proteins. Furthermore, the detection reagent may not be proteinaceous at all, but have chemical reactivity for its target analyte, e.g., boronic acids that react with cis-diols in glycoproteins or maleimides reagents the react with thiols. Broadly, a reagent is able to bind to and make a stable, although possibly fleeting and reversible, interaction with a target through interactions that include, but are not limited to, covalent, non-covalent, ionic, hydrogen bonding, pi-pi stacking, base pairing, or van der Waals interactions. It is also realized detection reagents may be aptamers, aptamer switches, single or double stranded nucleic acids, PNA (protein nucleic acids, gamma and bis), LNA (locked nucleic acids), or the like (i.e., a protein-nucleic acid hybrid).

As used herein, "actionable output" means a machine- or human-readable guidance including training changes, rest windows, imaging/referral prompts, re-test timing, and/or selection of supplementation categories with optional dosage/timing fields.

As used herein, "ratiometric measure" means a quantity formed by dividing the value of one biomarker (or composite/index thereof) by the value of another biomarker, reference, internal control, or subject-specific baseline, optionally after normalization or monotonic transformation (e.g., log, scaling), to yield a typically dimensionless feature. The term includes simple pairwise ratios (e.g., CK/AST, SAA/CRP), ratios of sums or weighted composites across categories, and fold-change ratios comparing a current value to a prior value for the same subject; it may be expressed as a raw ratio, percentage, or log-ratio and is used to reduce matrix/dilution and inter-subject variability and to enhance interpretive discrimination in the panel.

As used herein, "physiologic axis" means a non-limiting grouping of biomarkers that report on a common biological process, pathway, tissue/system state, or clinical construct (e.g., inflammation, muscle/tissue injury, trauma/stress, oxidative/joint status), and includes the listed biomarkers and their functional equivalents.

All elements and embodiments disclosed herein are intended to be combinable unless mutually inconsistent, and the written description and enablement extend to every such combination.

The foregoing description of the embodiments of the disclosure has been presented for the purposes of illustration and description. Each and every page of this submission, and all contents thereon, however characterized, identified, or numbered, is considered a substantive part of this application for all purposes, irrespective of form or placement within the application. This specification is not intended to be exhaustive or to limit the disclosure to the precise form disclosed. Many modifications and variations are possible in light of this disclosure.

All definitions, as defined and used herein, should be understood to control over dictionary definitions, definitions in documents incorporated by reference, and/or ordinary meanings of the defined terms.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

What is claimed is:

1. A multiplex biomarker panel, comprising:

a solid-phase substrate comprising a plurality of spatially discrete capture regions arranged as a multiplexed array; and an assay reagent set including a plurality of distinct affinity reagents, each affinity reagent immobilized at a respective one of the spatially discrete capture regions and each having specific binding affinity for a corresponding biomarker;

wherein the spatially discrete capture regions are arranged to enable simultaneous quantitative detection, in a single assay run, of a plurality of biomarkers from a single biological sample, the plurality of biomarkers comprising: C-reactive protein (CRP), serum amyloid A (SAA), interleukin-6 (IL-6), calprotectin (S100A8/A9), interferon regulatory factor 7 (IRF7), lactate, creatine kinase (CK), aspartate transaminase (AST), lactate dehydrogenase (LDH), myoglobin, disintegrin and metalloproteinase domain-containing protein 12 (ADAM-12), high-mobility group box 1 (HMGB1), haptoglobin, cortisol, 8-isoprostane, cartilage oligomeric matrix protein (COMP), matrix-metallopeptidase-3 (MMP-3), matrix metallopeptidase-8 (MMP-8) and ferritin.

2. The panel of claim 1, wherein the assay reagent set comprises, for each of the plurality of biomarkers, at least one of: an antibody capture reagent, an antibody or antibody fragment detection reagent, an aptamer or aptamer-switch element, or a particle-conjugated detection reagent.

* * * * *